United States Patent [19]

Petraitis

[11] Patent Number: 5,217,983

[45] Date of Patent: Jun. 8, 1993

[54] (N-BENZYL) ACETALDEHYDE BICYCLIC HETEROCYCLES USEFUL AS TOPICAL ANTIINFLAMMATORIES

[75] Inventor: Joseph J. Petraitis, Glenmoore, Pa.

[73] Assignee: Du Pont Merck Pharmacuetical Company, Wilmington, Del.

[21] Appl. No.: 860,775

[22] Filed: Mar. 27, 1992

[51] Int. Cl.$^5$ .................. A61K 31/41; C07D 249/18
[52] U.S. Cl. .................................. 514/359; 548/259; 548/261
[58] Field of Search ............. 514/359; 548/259, 261

[56] References Cited

U.S. PATENT DOCUMENTS

| 3,567,721 | 3/1971 | Wajngurt | 260/247.2 |
| 3,625,997 | 12/1971 | Basel | 260/247.2 |
| 3,725,431 | 4/1973 | Gschwend | 260/310 C |
| 3,930,005 | 12/1975 | Wejmar et al. | 424/253 |
| 4,088,654 | 4/1978 | Denzel et al. | 260/295.5 B |

FOREIGN PATENT DOCUMENTS

| 178178A | 4/1986 | European Pat. Off. |
| 179619 | 4/1986 | European Pat. Off. |
| 199543 | 10/1986 | European Pat. Off. |
| 284686A | 10/1988 | European Pat. Off. |
| 48-44253 | 2/1973 | Japan . |
| 2081708 | 2/1982 | United Kingdom . |

Primary Examiner—Patricia L. Morris

[57] ABSTRACT (Indol-1'-ylmethyl)-, (Indazol-1'-ylmethyl)-, (Benzimidazol-1'-ylmethyl)-, and (Benzotriazol-1'-ylmethyl)- phenylacetaldehydes as Topical Antiinflammatories.

9 Claims, No Drawings

(N-BENZYL) ACETALDEHYDE BICYCLIC HETEROCYCLES USEFUL AS TOPICAL ANTIINFLAMMATORIES

BACKGROUND OF THE INVENTION

1. Field of Invention

This invention relates to novel (N-benzyl)acetaldehyde bicyclic heterocycles, pharmaceutical compositions containing them, and methods of using them to treat skin inflammation, for example psoriasis, in mammals.

2. Background

Many diseases of the skin and muco-epithelia, such as psoriasis, are characterized by an inflammatory reaction in the underlying connective tissue and a hyperplasia (increased mitotic activity) of the overlying epithelia. Agents which suppress either or both the inflammatory and mitotic activity of the epithelia are effective in treating diseases of the skin.

The current treatment for skin and mucoepithelial diseases (i.e. psoriasis and chronic dermatitis) is primarily based upon topical steroids. These are efficacious but have significant side effects such as skin atrophy, rosacea and adrenal suppression and thus are limited in their chronic usage.

A second common treatment for psoriasis is the use of coal tar or its derivatives. This treatment is unpleasant, not very effective and has potential for carcinogenesis. For moderate to severe cases of psoriasis, psoralens with UVA or drugs such as methotrexate or cyclosporin A, whose side effects are kidney failure or liver toxicity, have been used with success.

A clear need exists for better treatment of skin diseases, particularly treatments which can provide at the same time effective, safe and cosmetically acceptable results. The compounds of this invention offer promise for providing such treatment.

SUMMARY OF THE INVENTION

This invention relates (N-benzyl)acetaldehyde bicyclic heterocycles useful as topical antiinflammatories. More specifically, the invention relates to (indol-1'-ylmethyl)-, (indazol-1'-ylmethyl)-, (benzimidazol-1'-ylmethyl)-, and (benzotriazol-1'-ylmethyl)-phenylacetaldehydes, pharmaceutical compositions containing them, and methods of using them to topically treat skin inflammation in mammals. These compounds have the general formula:

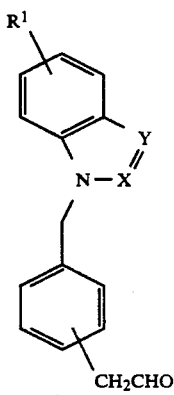

(I)

wherein

X and Y independently are CH or N;

$R^1$ is H, F, Cl, Br, $C_1$–$C_4$ alkyl, phenyl, benzyl, or $OR^2$ where $R^2$ is $C_1$–$C_4$ alkyl;

provided that when $R^1$ is other than H, $R^1$ is other than at the 7-position;

when X and Y are N and $R^1$ is other than H, $R^1$ is at the 4-position;

when X is CH and Y is N, $R^1$ is other than F; and when X and Y are N, $R^1$ is other than Br, F, phenyl or benzyl.

Preferred compounds of formula (I) are those in which the —$CH_2CHO$ group is present at the paraposition of the designated aromatic ring. Also preferred are those compounds of formula (I) in which X is CH and Y is N, X is N and Y is CH, or X and Y are both N.

Illustrative of the most preferred compounds of formula (I) are the following:

4-(benzimidazol-1'-ylmethyl)phenylacetaldehyde
4-(indazol-1'-ylmethyl)phenylacetaldehyde
4-(benzotriazol-1'-ylmethyl)phenylacetaldehyde

DETAILED DESCRIPTION

The compounds of formula (I) can be prepared according to the general synthetic route outlined in Scheme 1. Thus, compounds of formula (II) can be treated with an appropriate base, for example potassium hydride, followed by treatment with an appropriate alpha-bromotolunitrile. The resulting compounds of formula (III) can then be reduced using diisobutylaluminum hydride (DIBAH) followed by treatment with dilute acid, for example acetic acid, to provide compounds of formula (IV). Treatment of (IV) with base-treated (methoxymethyl)triphenylphosphonium chloride can provide compounds of formula (V). Treatment of compounds of formula (V) with mercuric acetate followed by dilute, aqueous potassium iodide results in formation of compounds of formula (I).

The compounds of formula (II), if not commercially available, can be obtained by one skilled in the art. Thus, compounds of formula (II), in which X and Y are CH, can be prepared by following the procedures and methods outlined in the "The Chemistry of Heterocyclic Compounds: Indoles," Vol. 25 (Part 1), Wiley-Interscience, New York, 1972. Similarly, the compounds of formula (II), in which X is nitrogen and Y is CH, can be prepared by methods described in "The Chemistry of Heterocyclic Compounds: Pyrazoles, Pyrazolines, Pyrazolidines, Indazoles and Condensed Rings," Vol. 22, pp. 289–382, Interscience Publishers, New York, 1967. Also, the compounds of formula (II), in which X is CH and Y is nitrogen, can be prepared by procedures outlined in "The Chemistry of Heterocyclic Compounds: Benzimidazoles and Congeneric Tricyclic Compounds," Vol. 40 (Part 1), pp. 1–285, John Wiley and Sons; Interscience, New York, 1981. Finally, the compounds of formula (II), in which X and Y are nitrogen, can be prepared by one skilled in the art from the procedures described by Phillip H. Morgan and Karl F. Hussung, *Trans. Ky. Acad. Sci.* 39 (1-2), 23–30 (1978) for $R_1$=4—Cl; Curt Wentrup and Wilfred D. Crow, *Tetrahedron* 26 (16), 3965 (1970) for $R_1$=4—Me; and R. Lawrence and Eric S. Wright, *Org. Mass Spectrom.* 3 (3), 367-77 (1970) for $R_1$=4—OMe.

Scheme 1

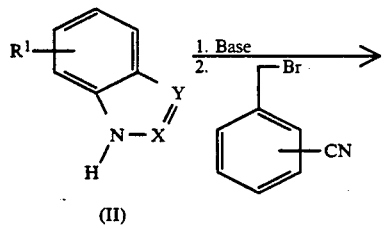
(II)

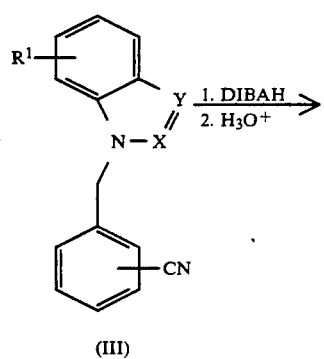
(III)

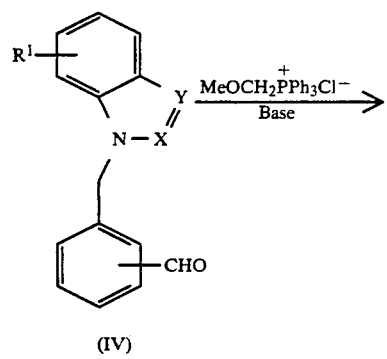
(IV)

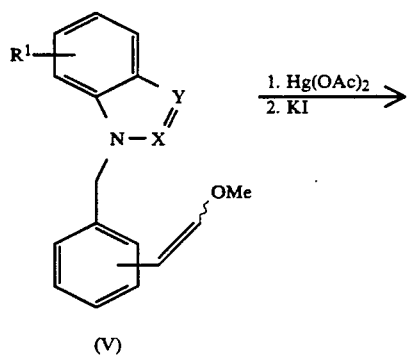
(V)

-continued
Scheme 1

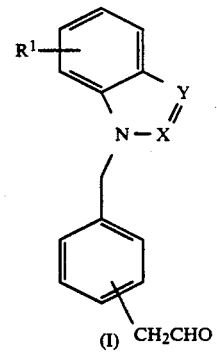
(I) CH₂CHO

EXAMPLES

Example 1

Part A: 4-(benzimidazol-1'-ylmethyl)benzonitrile

A mixture of 11.45 g (100 mmol) of potassium hydride (35% dispersion in oil) and 150 mL dry tetrahydrofuran was stirred at room temperature under nitrogen. Added portionwise was 11.80 g (100 mmol) of benzimidazole and the mixture stirred 10 minutes. Added next was 25.0 g (125 mmol) alpha-bromo-p-tolunitrile, dropwise in 75 mL dry tetrahydrofuran, and the mixture stirred at reflux for 2 hours. The reaction was allowed to cool to room temperature and carefully quenched with 5 mL of absolute methanol. The mixture was poured into 150 mL of water and extracted with 3 x 200 mL ethyl acetate. The organic layers were combined, dried (anhydrous magnesium sulfate), filtered and solvent was removed. The residue was purified by flash chromatography on silica gel using a mixture of ethyl acetafe - hexanes - acetic acid (80:18:2) as eluant. Obtained was 18.6 g (79.8 mmol, 79.8%) of 4-(benzimidazol-1'-ylmethyl)benzonitrile, mp=90°-92° C. (Nujol): 2229 cm$^{-1}$. High resolution mass spectrum: Calculated; 233.0953. Measured; 233.0955.

Part B: 4-(benzimidazol-1'-ylmethyl)benzaldehyde

A mixture of 10.6 g (45.0 mmol) 4-(benzimidazol-1'-ylmethyl)benzonitrile and 200 mL toluene was stirred at −78° C. under nitrogen. Added dropwise was 45 mL (67.5 mmol) of 1.5 M (in toluene) diisobutylaluminum hydride and the mixture was stirred at −78° C. for 2 hours followed by stirring at room temperature overnight. Carefully added was 100 mL of 5% acetic acid and the solution was stirred for 5 minutes at room temperature. The mixture was carefully neutralized with saturated sodium bicarbonate and extracted with 3 × 200 mL ethyl acetate. The organic layers were combined, dried (anhydrous magnesium sulfate), filtered and solvent was removed. The residue was purified by flash chromatography on silica gel using a mixture of ethyl acetate - hexanes - acetic acid (80:18:2) as eluant. Obtained was 6.5 g (27.5 mmol, 61.2%) of 4-(benzimidazol-1'-ylmethyl)benzaldehyde as a liquid. NMR (CDCl₃/TMS): δ5.4 (s, 2H), 7.1–7.8 (m, 8H), 8.0 (s, 1H). IR (Neat): 1694 cm$^{-1}$. High resolution mass spectrum: Calculated; 236.0949. Measured; 236.0959.

Part C: Mixture of (E)- and (Z)-1-(benzimidazol-1'-ylmethyl)-4-(2''-methoxyethenyl)benzene A mixture of 4.27 g (37.0 mmol) potassium hydride (35% dispersion in oil) and 150 mL dry tetrahydrofuran was stirred at room temperature under nitrogen. Added portionwise was 12.85 g (37.0 mmol) of (methoxymethyl)triphenylphosphonium chloride and the mixture stirred for 10 minutes. Added dropwise, in 25 mL dry tetrahydrofuran, was 4.0 g (17.0 mmol) of 4-(benzimidazol-1'-ylmethyl)benzaldehyde and the mixture stirred at reflux for 3 hours followed by stirring at room temperature overnight. The reaction was carefully quenched with 5 mL absolute methanol and poured into 150 mL of water. The mixture was extracted with 3 × 100 mL ethyl acetate and the organic layers were combined, dried (anhydrous magnesium sulfate), filtered and solvent was removed. The residue was purified by flash chromatography on silica gel using ethyl acetate as eluant. Obtained was 4.02 g (15.23 mmol, 89.6%) of a mixture of (E)- and (Z)-1-(benzimidazol-1'-ylmethyl)-4-(2''-methoxyethenyl)benzene as a liquid. NMR (CDCl$_3$/TMS): δ3.65 (2s, 3H), 5.25 (2s, 2H), 5.1–7.0 (m, 2H), 7.0–7.9 (m, 9H). IR (Nujol): 2923 cm$^{-1}$; High resolution mass spectrum: Calculated; 264.1263. Measured; 264.1264.

Part D: 4-(benzimidazol-1'-ylmethyl)phenylacetaldehyde

A mixture of 3.5 g (13.28 mmol) of a mixture of (E)- and (Z)-1-(benzimidazol-1'-ylmethyl)-4-(2''-methoxyethenyl)benzene, 340 mL tetrahydrofuran and 34 mL water was heated at reflux under nitrogen to purge the system free of oxygen. The mixture was allowed to cool to room temperature and added at once was 12.66 g (39.71 mmol) mercuric acetate and the solution stirred for one hour. The mixture was poured into 1000 mL of 7% potassium iodide solution and extracted with 3 × 400 mL benzene. The combined organic layers were then washed sequentially with 200 ml of 7% potassium iodide solution, 200 mL water and 200 mL brine. The organic layer was dried (anhydrous magnesium sulfate), filtered and solvent was removed. The residue was purified by flash chromatography on silica gel using a mixture of hexanes-ethyl acetate-methanol (55:35:10) as eluant. Obtained was 750 mg (3.00 mmol, 22.6%) of 4-(benzimidazol-1'-ylmethyl)phenylacetaldehyde as a liquid. NMR (CDCl$_3$/TMS): δ3.7 (d, 2H), 5.4 (s, 2H), 7.25–7.9 (m, 8H), 7.95 (s, 1H), 9.75 (t, 1H). IR (Neat): 1720 cm$^{-1}$. High resolution mass spectrum: Calculated; 250.1106. Measured; 250.1124.

Example 2

Part A: 4-(indazol-1'-ylmethyl)benzonitrile

A mixture of 960 mg (8.40 mmol) of potassium hydride (35% dispersion in oil) and 20 mL dry tetrahydrofuran was stirred at room temperature under nitrogen. Added portionwise was 1.0 g (8.40 mmol) of indazole and the mixture stirred 5 minutes. Added next was 2.15 g (11.00 mmol) alpha-bromo-p-tolunitrile, dropwise in 5 mL dry tetrahydrofuran, and the mixture stirred at room temperature for 2 days. The reaction was carefully quenched with 1 mL of absolute methanol, poured into 50 mL water, and extracted with 3 × 50 mL ethyl acetate. The organic layers were combined, dried (anhydrous magnesium sulfate), filtered and solvent was removed. The residue was purified by flash chromatography on silica gel using a mixture of hexanes - ethyl acetate (2:1) as eluant. The less polar of the two major fractions was isolated to provide 1.04 g (4.46 mmol, 53%) of 4-(indazol-1'-ylmethyl)benzonitrile, mp=72°–73° C. NMR (CDCl$_3$/TMS): δ5.65 (s, 2H), 7.15–7.8 (m, 8H), 8.05 (s, 1H). IR (Nujol): 2230 cm$^{-1}$. High resolution mass spectrum: Calculated ; 233.0953. Measured; 233.0955. The more polar of the two major fractions was also isolated to provide 600 mg (2.58 mmol, 30.6%) of 4-(indazol-2'-ylmethyl)benzonitrile as a liquid. NMR (CDCl$_3$/TMS): δ5.65 (s, 2H), 7.05–7.75 (m, 8H), 7.95 (s, 1H). IR (Neat): 2230 cm$^{-1}$. High resolution mass spectrum: Calculated; 233.0953. Measured; 233.0952. The two positional isomers described above were differentiated based on NMR as described for similarly substituted indazoles by Elguero, et al. (*Bull. Soc. Chim. Fr.* 6, 2075 (1966)).

Part B: 4-(indazol-1'-ylmethyl)benzaldehyde

A mixture of 10.0 g (42.0 mmol) 4-(indazol-1'-ylmethyl)benzonitrile and 250 mL toluene was stirred at −78° C. under nitrogen. Added dropwise was 42 mL (60.0 mmol) of 1.5M (in toluene) diisobutylaluminum hydride and the mixture was stirred at −78° C. for 2 hours followed by stirring at room temperature overnight. Carefully added was 100 mL of 5% acetic acid and the solution stirred for 5 minutes at room temperature. The mixture was carefully neutralized with saturated sodium bicarbonate and extracted with 3 × 200 mL ethyl acetate. The organic layers were combined, dried (anhydrous magnesium sulfate), filtered and solvent was removed. The residue was purified by flash chromatography on silica gel using a mixture of hexanes - ethyl acetate (2:1) as eluant. Obtained was 7.6 g (32.2 mmol, 76.6%) of 4-(indazol-1'-ylmethyl)benzaldehyde as a liquid. NMR (CDCl$_3$/TMS): δ5.7 (s, 2H), 7.15–7.85 (m, 8H), 8.1 (s, 1H), 9.95 (s, 1H). IR (Neat): 1695 cm$^{-1}$. High resolution mass spectrum: Calculated; 236.0949. Measured; 236.0950.

Part C: Mixture of (E)- and (Z)-1-(indazol-1'-ylmethyl)-4-(2''-methoxyethenyl)benzene A mixture of 8.09 g (70.0 mmol) potassium hydride (35% dispersion in oil) and 300 mL dry tetrahydrofuran was stirred at room temperature under nitrogen. Added portionwise was 24.37 g (70.0 mmol) of (methoxymethyl)triphenylphosphonium chloride and the mixture stirred for 10 minutes. Added dropwise in 50 mL dry tetrahydrofuran was 7.6 g (31.0 mmol) of 4-(indazol-1'-ylmethyl)benzaldehyde and the mixture was stired at reflux for 3 hours followed by stirring at room temperature for 2 days. The reaction was carefully quenched with 5 mL absolute methanol and poured into 300 mL of water. The mixture was extracted with 3 × 200 mL ethyl acetate and the organic layers were combined, dried (anhydrous magnesium sulfate), filtered and solvent was removed. The residue was purified by flash chromatography on silica gel using a mixture of hexanes - ethyl acetate (4:1) as eluant. Obtained was 3.90 g (14.77 mmol, 47.6%) of a mixture of (E)- and (Z)-1-(indazol-1'-ylmethyl)-4-(2''-methoxyethenyl) benzene as a liquid. NMR (CDCl$_3$/TMS): δ3.7 (2s, 3H), 5.55 (2s, 2H), 5.15–6.15 (m, 2H), 6.95–8.05 (m, 9H), IR (Neat): 2933 cm$^{-1}$. High resolution mass spectrum: Calculated; 264.1263. Measured; 264.1252.

Part D 4-(indazol-1'-ylmethyl)phenylacetaldehyde

A mixture of 3.5 g (13.28 mmol) of a mixture of (E)- and (Z)-1-(indazol-1'-ylmethyl)-4-(2''-methoxyethenyl)benzene, 340 mL tetrahydrofuran and 35 mL water was heated at reflux under nitrogen to purge the system free of oxygen. The mixture was allowed to cool to room temperature and added at once was 12.66 g (39.71 mmol) mercuric acetate and the solution stirred for one hour. The mixture was poured into 1000 mL of 7% potassium iodide solution and extracted with 3 × 400 mL benzene. The combined organic layers were then washed sequentially with 200 mL of 7% potassium iodide solution, 200 mL water and 200 mL brine. The organic layer was dried (anhydrous magnesium sulfate), filtered and solvent was removed. The residue was purified by flash chromatography on silica gel using a mixture of hexanes - ethyl acetate (2:1) as eluant. Obtained was 450 mg (1.8 mmol, 13.6%) of 4-(indazol-1'-ylmethyl)phenylacetaldehyde, mp=57°-58° C. NMR (CDCl$_3$/TMS): $\delta$3.6 (d, 2H), 5.55 (s, 2H), 7.05-7.3 (m, 7H), 7.7 (d, 1H), 8.0 (s, 1H), 9.65 (t, 1H). IR (Nujol): 1721 cm$^{-1}$. Mass spectrum: m/z=251 (M+H)$^+$.

Example 3

Part A: 4-(benzotriazol-1'-ylmethyl)benzonitrile

A mixture of 9.5 g (83.0 mmol) of potassium hydride (35% dispersion in oil) and 200 mL dry tetrahydrofuran was stirred at room temperature under nitrogen. Added portionwise was 10.0 g (83.0 mmol) of benzotriazole and the mixture stirred 10 minutes. Added next was 18.1 g (92.0 mmol) alpha-bromo-p-tolunitrile, dropwise in 100 mL dry tetrahydrofuran, and the mixture heated and stirred at reflux overnight. The mixture was allowed to cool to room temperature and carefully quenched with 5 mL absolute methanol. The solution was poured into 300 mL water and extracted with 3 × 200 mL ethyl acetate. The organic layers were combined, dried (anhydrous magnesium sulfate), filtered and solvent was removed. The residue was purified by flash chromatography on silica gel using a mixture of hexanes - ethyl acetate (2:1) as eluant. Obtained was 10.2 g (43.6 mmol, 52.5%) of 4-(benzotriazol-1'-ylmethyl)benzonitrile, mp =144°-147° C. NMR (CDCl$_3$/TMS): $\delta$5.9 (s, 2H), 7.3-7.7 (m, 7H), 8.15 (d, 1H). IR (Nujol): 2225 cm$^{-1}$. High resolution mass spectrum: Calculated; 234.0905. Measured; 234.0908.

Part B: 4-(benzotriazol-1'-ylmethyl)benzaldehyde

A mixture of 9.8 g (41.88 mmol) 4-(benzotriazol-1'-ylmethyl)benzonitrile and 250 mL toluene was stirred at −78° C. under nitrogen. Added dropwise was 42 mL (60.0 mmol) of 1.5 M (in toluene) diisobutylaluminum hydride and the mixture stirred at −78° C. for 2 hours followed by stirring at room temperature overnight. Carefully added was 100 mL of 5% acetic acid and the solution stirred for 5 minutes at room temperature. The mixture was carefully neutralized with saturated sodium bicarbonate and extracted with 3 × 200 mL ethyl acetate. The organic layers were combined, dried (anhydrous magnesium sulfate), filtered and solvent was removed. The residue was purified by flash chromatography on silica gel using a mixture of hexanes - ethyl acetate (1:1) as eluant. Obtained was 7.0 g (29.54 mmol, 70.5%) of 4-(benzotriazol-1'-ylmethyl)benzaldehyde, mp=133°-135° C. NMR (CDCl$_3$/TMS): $\delta$5.85 (s, 2H), 7.25-8.1 (m, 8H), 9.9 (s, 1H). IR (Nujol): 1688 cm$^{-1}$. High resolution mass spectrum: Calculated; 237.0902. Measured; 237,0905.

Part C: Mixture of (E)- and (Z)-1-(benzotriazol-1'-ylmethyl)-4-(2''-methoxyethenyl)benzene A mixture of 7.21 g (63.0 mmol) of potassium hydride (35% dispersion in oil) and 250 mL dry tetrahydrofuran was stirred at room temperature under nitrogen. Added portionwise was 21.59 g (63.0 mmol) of (methoxymethyl)triphenylphosphonium chloride and the mixture stirred at room temperature for 10 minutes. Added next was 6.8 g (28.0 mmol) of 4-(benzotriazol-1'-ylmethyl)benzaldehyde in 50 mL dry tetrahydrofuran. The mixture was heated at reflux for 3 hours, allowed to cool to room temperature and stirred overnight. The reaction was quenched with 5 mL absolute methanol and was poured into 300 mL water. The mixture was extracted with 3 × 200 mL ethyl acetate. The organic layers were combined, dried (anhydrous magnesium sulfate), filtered and solvent was removed. The residue was purified by flash chromatography on silica gel using a mixture of hexanes-ethyl acetate (2:1) as eluant. Obtained was 3.20 g (12.1 mmol, 43.2%) of a mixture of (E)- and (Z)-1-(benzotriazol-1'-ylmethyl)-4-(2''-methoxyethenyl)benzene as a liquid. NMR (CDCl$_3$/TMS); $\delta$ 3.7 (2s, 3H), 5.8 (2s, 2H), 5.2-7.0 (m, 2H), 7.2-8.15 (m, 8H). IR (Neat): 2935 cm$^{-1}$. High resolution mass spectrum: Calculated; 265.1215. Measured; 265.1216.

Part D: 4-(benzotriazol-1'-ylmethyl)phenylacetaldehyde

A mixture of 284 mg (1.07 mmol) of a mixture of (E)- and (Z)-1-(benzotriazol-1'-ylmethyl)-4-(2''-methoxyethenyl)benzene, 27 mL tetrahydrofuran and 2 mL water was heated at reflux under nitrogen to purge the system free of oxygen. The mixture was allowed to cool to room temperature and added was 1.02 g (3.20 mmol) mercuric acetate and the mixture stirred for 45 minutes. The mixture was poured into 100 mL of 7% potassium iodide solution and then extracted with 3 × 75 mL benzene. The combined organic layers were then washed sequentially with 100 mL of 7% potassium iodide solution, 100 mL water and 100 mL brine. The organic layer was dried (anhydrous magnesium sulfate), filtered and solvent was removed. The residue was purified by flash chromatography on silica gel using a mixture of hexanes - ethyl acetate (3:2) as eluant. Obtained was 80 mg (0.319 mmol, 29.8%) of 4-(benzotriazol-1'-ylmethyl)phenylacetaldehyde, mp=100°-102° C. NMR (CDCl$_3$/TMS): $\delta$3.6 (d, 2H), 5.8 (s, 2H), 7.1-7.4 (m, 7H), 8.0 (d, 1H), 9.65 (t, 1H). IR (Nujol): 1714 cm$^{-1}$. High resolution mass spectrum: Calculated; 250.0980. Measured; 250.1000.

Using the procedures of Examples 1-3 and Scheme I and the references above, the following compounds shown in Table I can be prepared.

TABLE I

| Example | R$_1$ | —CH$_2$CHO position | X | Y |
| --- | --- | --- | --- | --- |
| 4 | H | ortho | CH | CH |
| 5 | 4-Me | ortho | CH | CH |
| 6 | 5-F | ortho | CH | CH |
| 7 | 6-Cl | ortho | CH | CH |
| 8 | 4-Br | ortho | CH | CH |
| 9 | 6-OMe | ortho | CH | CH |
| 10 | 4-Ph | ortho | CH | CH |
| 11 | 5-CH$_2$Ph | ortho | CH | CH |
| 12 | H | meta | CH | CH |

TABLE I-continued

| Example | R₁ | —CH₂CHO position | X | Y |
|---|---|---|---|---|
| 13 | 5-Me | meta | CH | CH |
| 14 | 6-F | meta | CH | CH |
| 15 | 4-Cl | meta | CH | CH |
| 16 | 5-Br | meta | CH | CH |
| 17 | 4-OMe | meta | CH | CH |
| 18 | 5-Ph | meta | CH | CH |
| 19 | 6-CH₂Ph | meta | CH | CH |
| 20 | H | para | CH | CH |
| 21 | 6-Me | para | CH | CH |
| 22 | 4-F | para | CH | CH |
| 23 | 5-Cl | para | CH | CH |
| 24 | 6-Br | para | CH | CH |
| 25 | 5-OMe | para | CH | CH |
| 26 | 6-Ph | para | CH | CH |
| 27 | 4-CH₂Ph | para | CH | CH |
| 28 | H | ortho | CH | N |
| 29 | 4-CH₂Ph | ortho | CH | N |
| 30 | H | meta | CH | N |
| 31 | 4-Me | meta | CH | N |
| 32 | 4-Br | meta | CH | N |
| 33 | 4-Ph | meta | CH | N |
| 34 | 4-Cl | para | CH | N |
| 35 | 4-OMe | para | CH | N |
| 36 | H | ortho | N | CH |
| 37 | 4-Me | ortho | N | CH |
| 38 | 5-F | ortho | N | CH |
| 39 | 4-Br | ortho | N | CH |
| 40 | 6-OMe | ortho | N | CH |
| 41 | 4-Ph | ortho | N | CH |
| 42 | 5-CH₂Ph | ortho | N | CH |
| 43 | H | meta | N | CH |
| 44 | 5-Me | meta | N | CH |
| 45 | 6-F | meta | N | CH |
| 46 | 4-Cl | meta | N | CH |
| 47 | 5-Br | meta | N | CH |
| 48 | 5-Ph | meta | N | CH |
| 49 | 6-CH₂Ph | meta | N | CH |
| 50 | 5-Me | para | N | CH |
| 51 | 6-F | para | N | CH |
| 52 | 4-Cl | para | N | CH |
| 53 | 5-Br | para | N | CH |
| 54 | 4-OMe | para | N | CH |
| 55 | 5-Ph | para | N | CH |
| 56 | 6-CH₂Ph | para | N | CH |
| 57 | H | ortho | N | N |
| 58 | H | meta | N | N |
| 59 | 4-Me | meta | N | N |
| 60 | 4-Cl | para | N | N |
| 61 | 4-OMe | para | N | N |

UTILITY

Anti-inflammatory activities of the investigational compounds were studied in murine skin using the following protocol. Edema was induced by tetradecanoyl phorbol acteate (TPA) (1 ug/ear) [Marks, F., Furstenberger, G., Kownatzki, E., *Prostaglandin E Mediated Stimulation of Mouse Epidermis in vivo by Divalent Cation Ionophore A23187 and by Tumor Promotor TPA*, Cancer Res. 1981, 41:696–702]. Male CF-1 (Charles River) 18–20 grams were used. Investigational compounds (in acetone at 100 ug/ear) were applied to one ear just prior to application of the inflammagen. Four hours after TPA application, edema was determined by comparing the weights of 6 mm punch biopsies from control (solvent) and inflammagen-treated ears. Percent inhibitions were calculated using standard equations. Results are shown in Table II below.

TABLE II

| Compound | % Inhibition |
|---|---|
| Example 1 (Part D) | 63 |
| Example 2 (Part D) | 98 |
| Example 3 (Part D) | 46 |

The test results in Table II above show that the compounds described herein effectively suppress the mitotic activity associated with mouse skin hyperplasia induced by TPA, indicative of efficacy in treating human skin and muco-epithelial diseases such as psoriasis (in all its forms), lichen planas, chronic eczema, icthyosis, pityriasis and chronic uticaria.

Dosage and Formulations

The compounds of formula (I) can be administered to treat skin and muco-epithelial diseases such as psoriasis (in all its forms), lichen planas, chronic eczema, icthyosis, pityriasis and chronic uticaria. These compounds may be administered by any means that produces contact of the active agent with the site of the disease on the body of a mammal. They can be administered by any suitable means available for use in conjunction with pharmaceuticals, either as individual therapeutic agents or in a combination with steroid drugs, particularly topical steroids such as Synalar (*fluocinolone acetonide*), Lidex (fluocinolone), Westcort (*hydrocortisone valerate*), Valisone (betamethasone valeate), and Diprasone (*betamethasone dipropionate*). They can be administered alone, but are generally administered with a pharmaceutical carrier according to standard pharmaceutical practice.

The dosage administered will, of course, vary depending upon known factors such as the pharmacodynamic characteristics of the particular agent, and its mode of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for topical administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered topically as an ointment, cream or lotion. Useful pharmaceutical dosage forms for the topical administration of the compound useful in this invention can be illustrated as follows:

Topical Formulations

An ointment for topical administration is prepared at 70° C. by adding the active ingredient to a mixture of 48% by weight white petrolatum, 10% liquid petrolatum, 8% glycerol monostearate, 3% isopropyl myristate and 20% lanolin. After thorough mixing, a warm solution of methyl and propyl parabens in water containing sodium acetone bisulfite is added such that the final concentrations of each paraben is 0.15%, of water is 8% and of sodium acetone bisulfite is 0.5%. The mixture is stirred until it has reached room temperature.

A cream for topical administration is prepared at 75° C. by adding the active ingredient to a mixture of 1% sodium lauryl sulfate, 12% propylene glycol, 25% stearyl alcohol, 25% white petrolatum and 37% water. The mixture is stirred until it congeals.

A gel for topical administration is prepared at 70° C. by adding the active ingredient to a mixture of 0.75% Carbopol 940 (polycarbopol), 46.25% water, 3% emulsifier hydroxylated lanolin, 50% ethanol and, optionally, 1-2% diisopropanolamine. The mixture is stirred until it cools to room temperature.

What is claimed is:

1. A compound of formula (I) which is

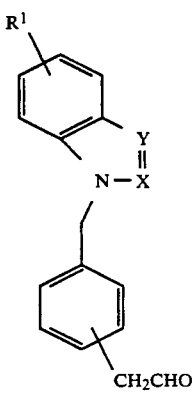

wherein

X and Y are N;

$R^1$ is H, Cl, $C_1$-$C_4$ alkyl, or $OR^2$ where $R^2$ is $C_1$-$C_4$ alkyl;

provided that when $R^1$ is other than H, $R^1$ is at the 4-position.

2. A compound of claim 1 having the formula

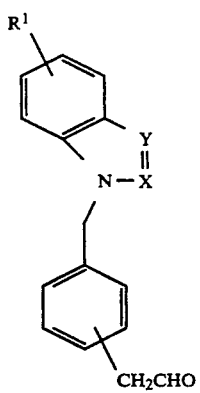

wherein

X and Y are N;

$R^1$ is H, Cl, $C_1$-$C_4$ alkyl, or $OR^2$ where $R^2$ is $C_1$-$C_4$ alkyl;

provided that when $R^1$ is other than H, $R^1$ is at the 4-position.

3. A compound of claim 2 which is 4-(benzotriazol-1'-ylmethyl) phenylacetaldehyde.

4. A topical pharmaceutical composition consisting essentially of a carrier suitable for topical formulation and an efficaceous amount of a compound having the formula:

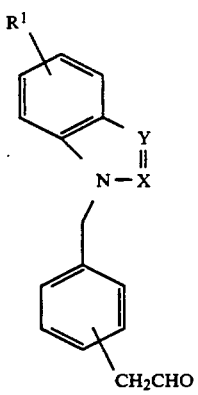

wherein

X and Y are N;

$R^1$ is H, Cl, $C_1$-$C_4$ alkyl, or $OR^2$ where $R^2$ is $C_1$-$C_4$ alkyl;

provided that when $R^1$ is other than H, $R^1$ is at the 4-position.

5. The topical composition of claim 4 wherein the compound has the formula:

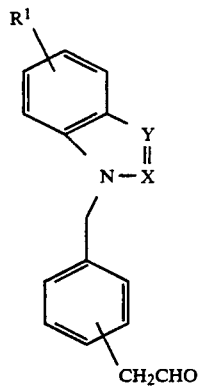

wherein

X and Y are N;

$R^1$ is H, Cl, $C_1$-$C_4$ alkyl, or $OR^2$ where $R^2$ is $C_1$-$C_4$ alkyl;

provided that when $R^1$ is other than H, $R^1$ is at the 4-position.

6. The topical composition of claim 5 wherein the compound is 4-(benzotriazol-1'-ylmethyl)-phenylacetaldehyde.

7. A method of treating a skin or mucoepithelial disease in a mammal comprising topically administering to the site of the disease on said mammal an efficaceous amount of a compound of the formula

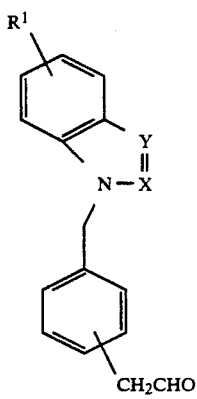

wherein
X and Y are N;
$R^1$ is H, Cl, $C_1$–$C_4$ alkyl, or $OR^2$ where $R^2$ is $C_1$–$C_4$ alkyl;
provided that
when $R^1$ is other than H, $R^1$ is at the 4-position.

8. The method of claim 7 wherein the compound has the formula

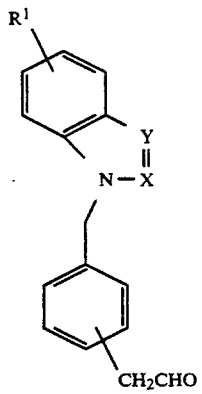

wherein
X and Y are N;
$R^1$ is H, Cl, $C_1$–$C_4$ alkyl, or $OR^2$ where $R^2$ is $C_1$–$C_4$ alkyl;
provided that
when $R^1$ is other than H, $R^1$ is at the 4-position.

9. The method of claim 7, wherein the compound of the formula administered is 4-(benzotriazol-4′-ylmethyl) phenylacetaldehyde.

* * * * *